United States Patent
Obel et al.

(10) Patent No.: US 7,058,451 B2
(45) Date of Patent: Jun. 6, 2006

(54) METHOD AND APPARATUS FOR DETERMINING DEPLETED CAPACITY OF A BATTERY

(75) Inventors: Martin Obel, Danderyd (SE); Jan Lindberg, Sollentuna (SE)

(73) Assignee: St. Jude Medical AB, Jarfalla (SE)

( * ) Notice: Subject to any disclaimer, the term of this patent is extended or adjusted under 35 U.S.C. 154(b) by 511 days.

(21) Appl. No.: 10/276,123

(22) PCT Filed: Dec. 6, 2001

(86) PCT No.: PCT/SE01/02726

§ 371 (c)(1),
(2), (4) Date: Nov. 13, 2002

(87) PCT Pub. No.: WO02/49718

PCT Pub. Date: Jun. 27, 2002

(65) Prior Publication Data

US 2003/0149455 A1    Aug. 7, 2003

(30) Foreign Application Priority Data

Dec. 19, 2000    (SE) ................................ 0004772.0

(51) Int. Cl.
*A61N 1/24* (2006.01)

(52) U.S. Cl. ........................... 607/27; 607/29; 320/132
(58) Field of Classification Search ............... 320/132, 320/149, 157, 161, 162; 607/27, 29
See application file for complete search history.

(56) References Cited

U.S. PATENT DOCUMENTS

| | | | |
|---|---|---|---|
| 4,725,784 A * | 2/1988 | Peled et al. | 324/427 |
| 5,391,193 A | 2/1995 | Thompson | |
| 5,769,873 A | 6/1998 | Zadeh | |
| 5,808,445 A * | 9/1998 | Aylor et al. | 320/132 |
| 6,037,778 A * | 3/2000 | Makhija | 324/433 |
| 6,094,052 A * | 7/2000 | Arai et al. | 324/428 |
| 6,108,579 A | 8/2000 | Snell et al. | |
| 6,586,130 B1 * | 7/2003 | Guiheen et al. | 429/50 |

FOREIGN PATENT DOCUMENTS

| | | |
|---|---|---|
| EP | 0 763 747 | 3/1997 |
| WO | WO 01/05466 | 1/2001 |

* cited by examiner

*Primary Examiner*—Robert E. Pezzuto
*Assistant Examiner*—Eric Bertram
(74) *Attorney, Agent, or Firm*—Schiff Hardin LLP

(57) ABSTRACT

In a method and apparatus for determining the depleted capacity of a $CF_x$ type battery used in an implantable medical device, average values of battery voltage and battery current drawn from the battery are measured during a measurement time, the length of which exceeds a battery voltage recovery time after a load change, and wherein the actual depleted capacity of the battery is determined by predetermined relations between combinations of the average values of voltage and current and depleted battery capacity.

15 Claims, 3 Drawing Sheets

Fig. 3

| Depleted capacity | 0.0 Ah | 0.05 Ah | 0.2 Ah | 0.4 Ah | 0.6 Ah | 0.8 Ah | 1.0 Ah | 1.1 Ah | 1.2 Ah |
|---|---|---|---|---|---|---|---|---|---|
| Average Load Current | Average load Voltage | | | | | | | | |
| 20 µA | 3.13 V | 2.98 V | 2.99 V | 2.98 V | 2.95 V | | | | |
| 30 µA | 3.080 V | 2.965 V | 2.975 V | 2.960 V | 2.840 V | 2.90 V | | | |
| 46 µA | 3.045 V | 2.95 V | 2.955 V | 2.845 V | 2.92 V | 2.88 V | 2.80 V | 2.72 V | 2.15 V |
| 90 µA | 2.95 V | 2.915 V | 2.92 V | 2.91 V | 2.89 V | 2.85 V | 2.775 V | 2.675 V | 2.20 V |

METHOD AND APPARATUS FOR DETERMINING DEPLETED CAPACITY OF A BATTERY

BACKGROUND OF THE INVENTION

1. Field of the Invention

The present invention relates to a method and an apparatus for determining depleted capacity of a battery of $CF_x$ type used in an implantable medical device.

2. Description of the Prior Art

So called $CF_x$ (carbon monoFluoride) batteries offer the possibility to use fast microprocessors in implantable medical devices like pacemakers, since this type of battery has the capability of delivering current pulses in the milliampere range required by most suitable microprocessors. Further, there is a growing interest in multi-chamber pacing and also in high rate pacing for arrhytmia suppression and termination which also increases the need of the battery to deliver higher battery current. Future products will require high speed and long range telemetry, which also requires higher battery current.

However, the determination of the state of discharge or remaining capacity of this kind of battery currently causes considerable difficulties, since there is no single electrical quantity which is well correlated to remaining usable battery capacity.

The battery voltage exhibits very long time constants after load changes and as a consequence there is no useful relation between the instantaneous battery voltage and the state of discharge or remaining battery capacity unless the battery load is constant. Measuring the battery impedance is not useful either for this purpose, since it does not provide useful data during the whole discharge period but only in the latter part of the battery lifetime. Thus, known conventional methods of determining the remaining capacity of batteries used in implantable medical devices cannot be used for $CF_x$ type of batteries.

SUMMARY OF THE INVENTION

An object of the present invention is to provide a new technique for determining the status of $CF_x$ type batteries, when used in implantable medical devices, especially implantable heart stimulators.

The above object is achieved in accordance with the principles of the present invention in a method and apparatus for determining the depleted capacity of a $CF_x$ type battery used in an implantable medical device, wherein average values of battery voltage and battery current drawn from the battery are measured during a measurement time, the length of which exceeds a battery voltage recovery time after a load change, and wherein the actual depleted capacity of the battery is determined by predetermined relations between combinations of the average values of voltage and current and depleted battery capacity.

Thus if the battery voltage and the current drawn for the battery are averaged over a sufficiently long periods these average values can be used for determining the remaining capacity of the battery. The voltage and current are averaged over a measurement time exceeding the length of a battery voltage recovery time after a load change, the measurement time exceeding the recovery time preferably by a predetermined factor between 5 and 10. The recovery time can be defined as the time needed for the battery voltage to reach a certain percentage, e.g. 90%, of its steady state level.

In another embodiment of the method according to the invention, the average values of voltage and current are entered into a predetermined look-up table providing depleted battery capacity for different average voltage and current combinations. In practice such a look-up table is available from e.g. the battery manufacturer Wilson Greatbatch based on constant current data. Experiments have, however, shown that if the battery voltage and current are averaged over a sufficiently long measurement time combinations of the average voltage and average current values can be used for obtaining reliable values of depleted battery capacity from such a table.

In other embodiments of the method according to the invention depleted battery capacity is also determined by time integrating the total current drawn from the battery. This technique for determining depleted battery capacity is per se previously known when applied to other types of batteries for implantable medical devices, see e.g. U.S. Pat. No. 5,769,873. According to the invention an alarm is preferably triggered if the difference between depleted battery capacities, determined from measured average values of battery voltage and current and determined by time integration of the current drawn from the battery, respectively, exceeds a predetermined threshold value. The triggering of the alarm then indicates that the depleted battery capacity has to be further considered or investigated.

In a further embodiment of the apparatus according to the invention the averaging unit is adapted to determine the average values by sampling and integrating battery voltage and current during the measurement time. As discussed above the measurement time is in practice comparatively long, e.g. 24 h, and the sampling frequency is chosen high enough to get good accuracy of the average values, e.g. a sampling frequency of 256 Hz. With the use of an optional filter in front of an analog to digital converter, the sampling frequency can be reduced, e.g. to the range 0.1 to 1 Hz.

In further embodiments of an apparatus according to the invention an impedance measurement unit is provided to measure the internal battery impedance when depleted battery capacity reaches a predetermined threshold value and a second determining unit is provided to thereafter determine depleted battery capacity from the measured internal impedance. Internal impedance measurements give reliable values of the depleted battery capacity only in the fatter part of the battery lifetime. A first triggering unit is therefore preferably provided to trigger the impedance measurement unit when depleted battery capacity reaches the predetermined threshold value, determined from measured average values of battery voltage and current as described above.

In another embodiment of the apparatus according to the invention a second triggering unit triggers an alarm if the difference between depleted battery capacities, determined from measured average values of battery voltage and current, and determined by time integration of the current drawn from the battery or determined from the measured internal impedance, respectively, exceeds a predetermined threshold value. Thus, if there are discrepancies in the depleted battery capacities determined by the different methods, this is indicated to the patient and/or the physician so that further investigations can be made. In this way improved security with reference to the battery status is obtained.

DESCRIPTION OF THE DRAWINGS

FIG. 3 illustrates an example of a look-up table suitable for use for determining depleted battery capacity in accordance with the invention.

DESCRIPTION OF THE PREFERRED EMBODIMENTS

Figure 1:
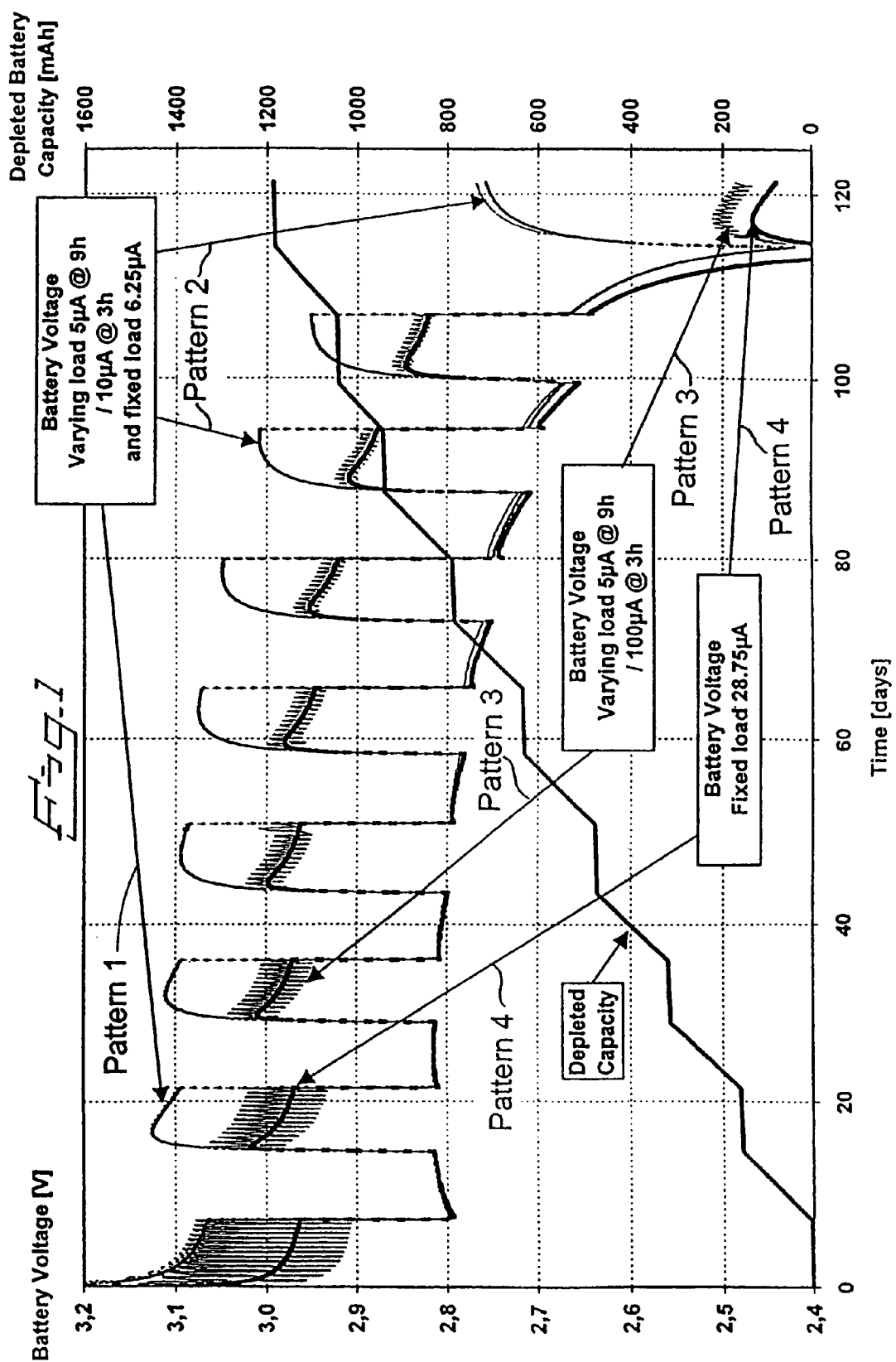
FIG. 1 is a plot of battery voltage and discharge capacity versus time obtained from measurements on a $CF_x$ type battery.

FIG. 1 is a plot of battery voltage and discharged capacity versus time obtained from measurements on a CFx type battery. The battery was subjected to different load patterns in a 17 weeks test sequence. More precisely FIG. 1 shows the results obtained for four different load patterns simulating various types of pacemaker loads.

Pattern 1 includes 3 hours of 10 μA load followed by 9 hours of 5 μA load, repeated 14 times, which gives a total time of 7 days. This pattern simulates a typical low current sequence with 3 hours of load threshold (Autocapture) single chamber pacing, followed by 9 hours of inhibition.

Pattern 2 includes a fixed load of 6.25 μA during 7 days, representing the average load of pattern 1.

Pattern 3 includes 3 hours of 100 μA load followed by 9 hours of 5 μA load, repeated 14 times, which gives a total time of 7 days. This simulates 3 hours of high threshold, multiple chambers pacing, followed by 9 hours of inhibition.

Pattern 4 includes a fixed load of 28.75 μA during 7 days, representing the average load of the pattern 3.

Between each week of loads simulating typical pacemaker loads according to patterns 1–4 above one week follows with a heavy load of approximately 900 μA in order to discharge the battery within a reasonably short time. In FIG. 1 such cycles are shown repeated 8 times. In FIG. 1 total depleted battery capacity is also showed as a function of time.

In FIG. 1 can be seen that the dynamic impedance is high in the beginning of the battery lifetime and then successively decreases. It can also be seen that the recovery time increases with the depletion of the battery. Thus at the time of about 60 days in FIG. 1 steady state is reached after a period of heavy load within a few days, whereas at time 100 days steady state is hardly reached within one week.

Figure 2:
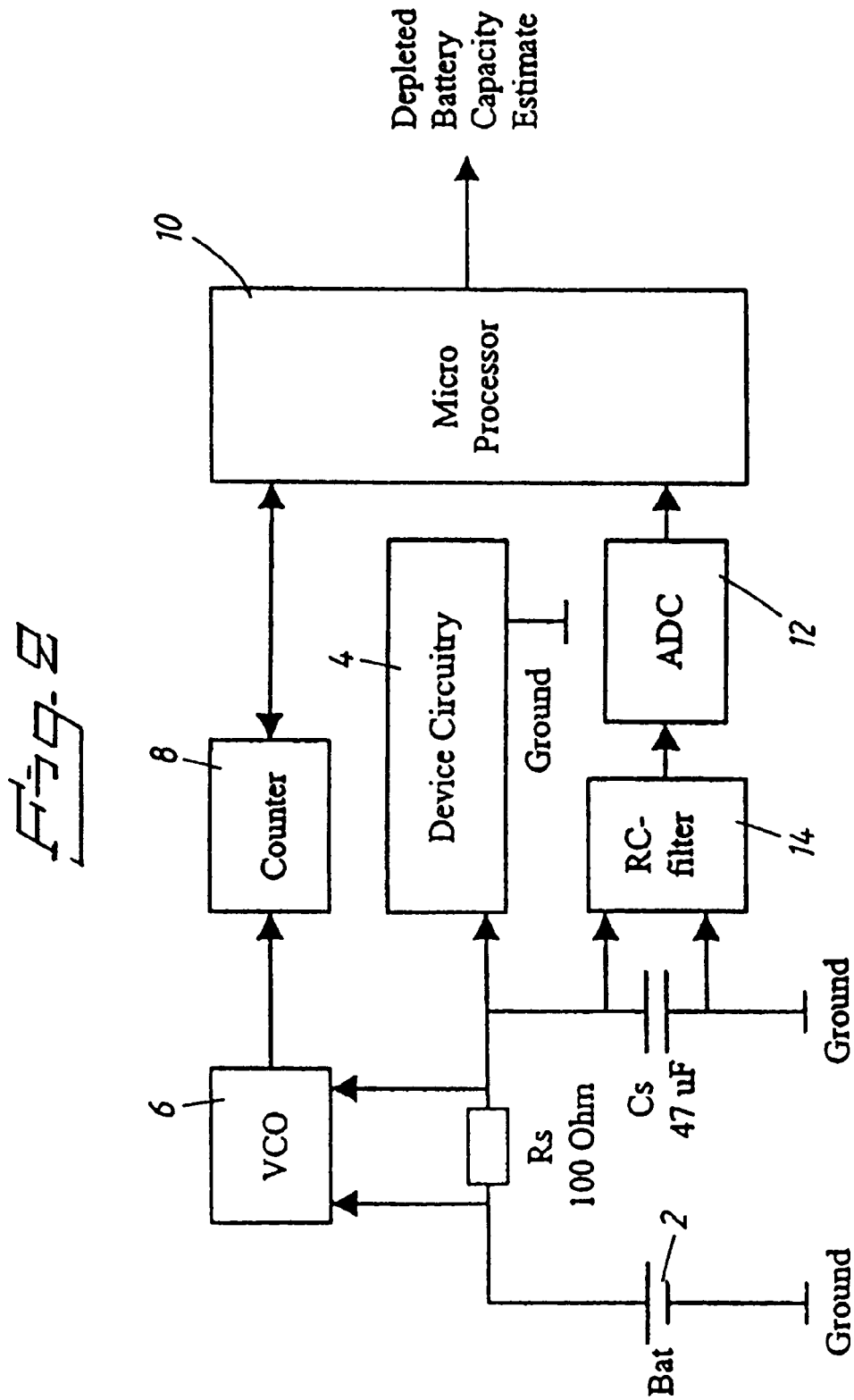
FIG. 2 is a block diagram of an embodiment of the apparatus according to the invention.

In FIG. 2 an embodiment is shown of the apparatus according to the invention implemented in a pacemaker.

A shunt resistor Rs typically of 100 Ohm is connected to the battery 2 of $CF_x$ type to be tested. This resistor Rs converts the current from the battery 2 to a voltage. The current drain from the battery 2 consists of the internal housekeeping current and the current used for therapeutic treatment, i.e. pacing pulses.

A voltage controlled oscillator (VCO) 6 converts the voltage across the resistor Rs to a pulse train with a frequency, which is proportional to the voltage.

The counter 8 counts the pulse train pulses from the VCO 6. The count is read by the microprocessor 10 every 24 hours. Thereafter the counter 8 is reset by the microprocessor 10 and starts counting for another 24 hours period.

A stabilizing capacitor Cs typically of 47 μF is used for stabilizing the supply voltage during varying battery current loads.

An analog to digital converter (ADC) 12, preceded by a RC-filter 14, converts the battery voltage to a digital word.

The microprocessor 10 controls the counter 8, reads the ADC 12 and calculates remaining capacity of the battery 2 as will be further explained in the following.

The device circuitry 4 represents the complete normal circuitry of the pacemaker.

The average battery voltage is determined over a period of 24 hours. The battery voltage is sampled by the ADC 12. The 24 hours average voltage is calculated by the microprocessor 10 by calculating the sum of all sampled digital values during 24 hours and then dividing this sum by the number of samples. The voltage is sampled with such a high frequency that good accuracy of the true average value is achieved, e.g. a sampling frequency of 1 Hz.

The average battery current is also calculated over a period of 24 hours. The current from the battery 2 is measured by measuring the voltage across the resistor Rs. The measured voltage is supplied to the VCO 6, which is generating a pulse train with a frequency proportional to the measured voltage, and consequently proportional to the current. This digital signal with a varying frequency is supplied to the counter 8. The counter value is read every 24 hours. The counter 8 is then immediately reset to be ready for counting during the following 24 hours period.

In the embodiment shown in FIG. 2 a VCO 6 is used for current measurements and an ADC 12 is used for voltage measurements. As alternatives either VCOs or ADCs can be used for both current and voltage measurements. As another alternative the microprocessor can be replaced by hard-wired logic.

The 24 hours average voltage and current values are entered into a lookup table as shown in FIG. 3 to obtain remaining battery capacity.

The table in FIG. 3 is an example based on constant load current data available from the battery manufacturer Wilson Greatbatch. However, experiments have shown that corresponding tables are valid for variable loads when using voltage and current average values determined as described above.

The table in FIG. 3 is used as follows. The average current for the last 24 hours is determined to e.g. 30 μA. The corresponding average voltage has been determined to e.g. 2.940 V. The 30 μA row is then followed in the table until the measured average voltage of 2.940 V is reached. This column in the table is followed to the top of the table where the depleted capacity can be read to 0.6 Ah. Interpolation is used to determine a value for the depleted capacity when one or both of the average voltage and the average load current values are in between the values in the table.

The look-up table is preferably stored in the memory of the microprocessor 10 and the described procedure is executed in automated fashion. The invention can then be used as a new advantageous RRT (Recommended Replacement Time) indicator for CFx type batteries.

Although modifications and changes may be suggested by those skilled in the art, it is the invention of the inventors to embody within the patent warranted heron all changes and modifications as reasonably and properly come within the scope of their contribution to the art.

The invention claimed is:

1. A method for determining depleted capacity of a $CF_x$ type battery in an implantable medical device, comprising the steps of:

measuring an average value of battery voltage and an average value of battery current drawn from a $CF_x$ type battery during a measurement time having a length exceeding a battery voltage recovery time of said $CF_x$ type battery after a load change; and determining actual depleted capacity of said $CF_x$ type battery from predetermined relationships between combinations of said average values of voltage and current and values of depleted capacity.

2. A method as claimed in claim 1 comprising measuring said average voltage and average current during a measurement time which exceeds said battery recovery time by a predetermined factor.

3. A method as claimed in claim 2 wherein said factor is between 5 and 10.

4. A method as claimed in claim 1 comprising measuring said average voltage and said average current from a $CF_x$ type battery having a battery recovery time in a range between 3 and 50 hours.

5. A method as claimed in claim 1 comprising measuring said average voltage and said average current for a measurement time exceeding 24 hours.

6. A method as claimed in claim 1 wherein the step of determining said actual depleted capacity comprises storing predetermined combinations of average voltage and average current, with respect to depleted battery capacity, in a look-up table, and consulting said look-up table to determine a depleted battery capacity therein corresponding to said combinations of said measured average voltage and said measured average current.

7. A method as claimed in claim 1 further comprising integrating current drawn from said $CF_x$ type battery over time, thereby obtaining an integrated current value, and also determining said actual depleted battery capacity from a relationship between depleted battery capacity and said integrated current value.

8. A method as claimed in claim 7 comprising triggering an alarm if a difference between the actual depleted battery capacity determined from said combination of average battery voltage and average battery current, and the actual depleted battery capacity determined from said integrated current value, exceeds a predetermined threshold value.

9. An apparatus for determining depleted capacity of a $CF_x$ type battery in an implantable medical device, comprising:
   an averaging unit adapted for connection to a $CF_x$ type battery for measuring an average value of voltage drawn from said $CF_x$ type battery and an average value of current drawn from said $CF_x$ type battery during a measurement time having a length exceeding a battery voltage recovery time of said $CF_x$ type battery after a load change; and
   a determining unit connected to said averaging unit for determining actual depleted battery capacity of said $CF_x$ type battery from predetermined relationships between combinations of said average values of voltage and current and depleted battery capacity.

10. An apparatus as claimed in claim 9 wherein said determining unit includes a look-up table wherein predetermined relationships between combinations of average battery voltage and average battery current and depleted battery capacity are stored, and wherein said determining unit consults said look-up table to determine a depleted battery capacity corresponding to said combinations of the measured average voltage and the measured average current.

11. An apparatus as claimed in claim 9 wherein said averaging unit determines said average value of battery voltage by sampling an integrating said battery voltage during said measurement time, and determines said average value of battery current by sampling and integrating said battery current during said measurement time.

12. An apparatus as claimed in claim 9 wherein said determining unit includes an integrating unit which integrates a total current drawn from said $CF_x$ type battery during said measurement time, to determine a total current depleted from said battery, and a second determining unit which also determine said actual depleted battery capacity from a relationship to said total current.

13. An apparatus as claimed in claim 12 comprising a triggering unit which triggers an alarm if a difference between said actual depleted battery capacity determined from said combinations of average values of voltage and current, and said actual depleted battery capacity determined from said total current, exceeds a predetermined threshold value.

14. An apparatus as claimed in claim 9 further comprising an impedance measurement unit which measures internal battery impedance of said $CF_x$ type battery when said actual depleted battery capacity reaches a predetermined threshold value determined from said measured average values of battery voltage and battery current, and further comprising a second determining unit which thereafter determines said actual depleted battery capacity from a relationship between depleted battery capacity and said measured internal impedance.

15. An apparatus as claimed in claim 14 further comprising a triggering unit which triggers an alarm if a difference between said actual depleted battery capacity determined from said combination of average values of battery voltage and battery current, and said actual depleted battery capacity measured integral impedance exceeds a predetermined threshold value.

* * * * *